US006663569B1

(12) United States Patent
Wilkins et al.

(10) Patent No.: US 6,663,569 B1
(45) Date of Patent: Dec. 16, 2003

(54) DIAGNOSTIC ULTRASOUND SYSTEM CART WITH VARIABLE ELEVATION CONTROL PANEL

(75) Inventors: Jay Wilkins, Belgrade, MT (US); Robert Mesaros, Bothell, WA (US); Yas Matsui, Redmond, WA (US); Randall Dean Lord, Mukilteo, WA (US); John Russell Murkowski, Seattle, WA (US); William Hollman, Lake Forest Park, WA (US); Ulrich Rankers, Livermore, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 16 days.

(21) Appl. No.: 10/154,733

(22) Filed: May 23, 2002

(51) Int. Cl.[7] ................................. A61B 8/00
(52) U.S. Cl. ..................................... 600/459
(58) Field of Search ................ 600/443, 447, 600/448, 449, 459, 460, 461, 432

(56) References Cited

U.S. PATENT DOCUMENTS

| | | | | |
|---|---|---|---|---|
| 4,625,731 A | * | 12/1986 | Quedens et al. | 600/443 |
| 4,870,954 A | | 10/1989 | Satoh | |
| 5,129,397 A | * | 7/1992 | Jingu et al. | 600/437 |
| 5,941,824 A | * | 8/1999 | Hwang | 600/437 |

* cited by examiner

Primary Examiner—Francis J. Jaworski
Assistant Examiner—Maulin Patel
(74) Attorney, Agent, or Firm—W. Brinton Yorks, Jr.

(57) ABSTRACT

A cart-borne ultrasound system is described which includes a portable cart holding the electronic circuitry of the ultrasound system, a control panel for controlling the ultrasound system, and a display. The control panel is supported by an articulating mechanism which enables the control panel to be raised and lowered to accommodate operators of different height, and enables the control panel to move toward and away from the user to accommodate users in the sitting or standing positions. In a preferred embodiment the articulating mechanism comprises a parallelogram-shaped linkage which also maintains a constant angle of inclination of the control panel as it is raised and lowered.

25 Claims, 9 Drawing Sheets

DIAGNOSTIC ULTRASOUND SYSTEM CART WITH VARIABLE ELEVATION CONTROL PANEL

This invention relates to ultrasonic diagnostic imaging systems and, in particular, to ultrasound systems with control panels that have an adjustable height.

Cart-borne ultrasound systems are intended to be operated by any diagnostician with the requisite training. This means that the ultrasound system may be used by some who are short in stature and others who are very tall. The system should adapt to people of different height. Otherwise, the operator may need to stretch, bend over, or otherwise contort to an uncomfortable position. Over time such contortions can lead to muscular or skeletal discomfort. To relieve these problems some manufacturers have designed the ultrasound system cart so that the control panel can be adjusted vertically. One simple approach is to hinge the control panel so that it will swing up and down. As it does so, however, it will assume a different angle at each elevational height. It is desirable for the control panel to maintain a constant angle to the operator so that the control panel is comfortable to use regardless of its elevation.

One way to maintain a constant angle is to elevate the entire control and display portion of the ultrasound system. Such an approach should take into consideration the posture of users of the ultrasound system when the control panel and display are elevated to different heights. In particular, an elevation system should provide positions of comfort for both standing and sitting users. It is desirable to provide a control panel for an ultrasound system which maintains a comfortable user angle to the operator and is comfortable for both sitting and standing users.

In accordance with the principles of the present invention a variable elevation control panel is provided for a cart-borne ultrasound system. The control panel is supported by an articulating mechanism by which the height of the control panel can be adjusted. Preferably the control panel maintains a comfortable angle of inclination as its height is changed. As the control panel is articulated vertically it simultaneously extends toward the user when lowered to better accommodate a sitting user, and extends back toward the cart when raised to better accommodate a standing user. In one embodiment the articulation mechanism is configured as a parallelogram-shaped linkage. In another embodiment the articulation mechanism raises and lowers the control panel at an acute angle to the vertical direction.

Figure 1:
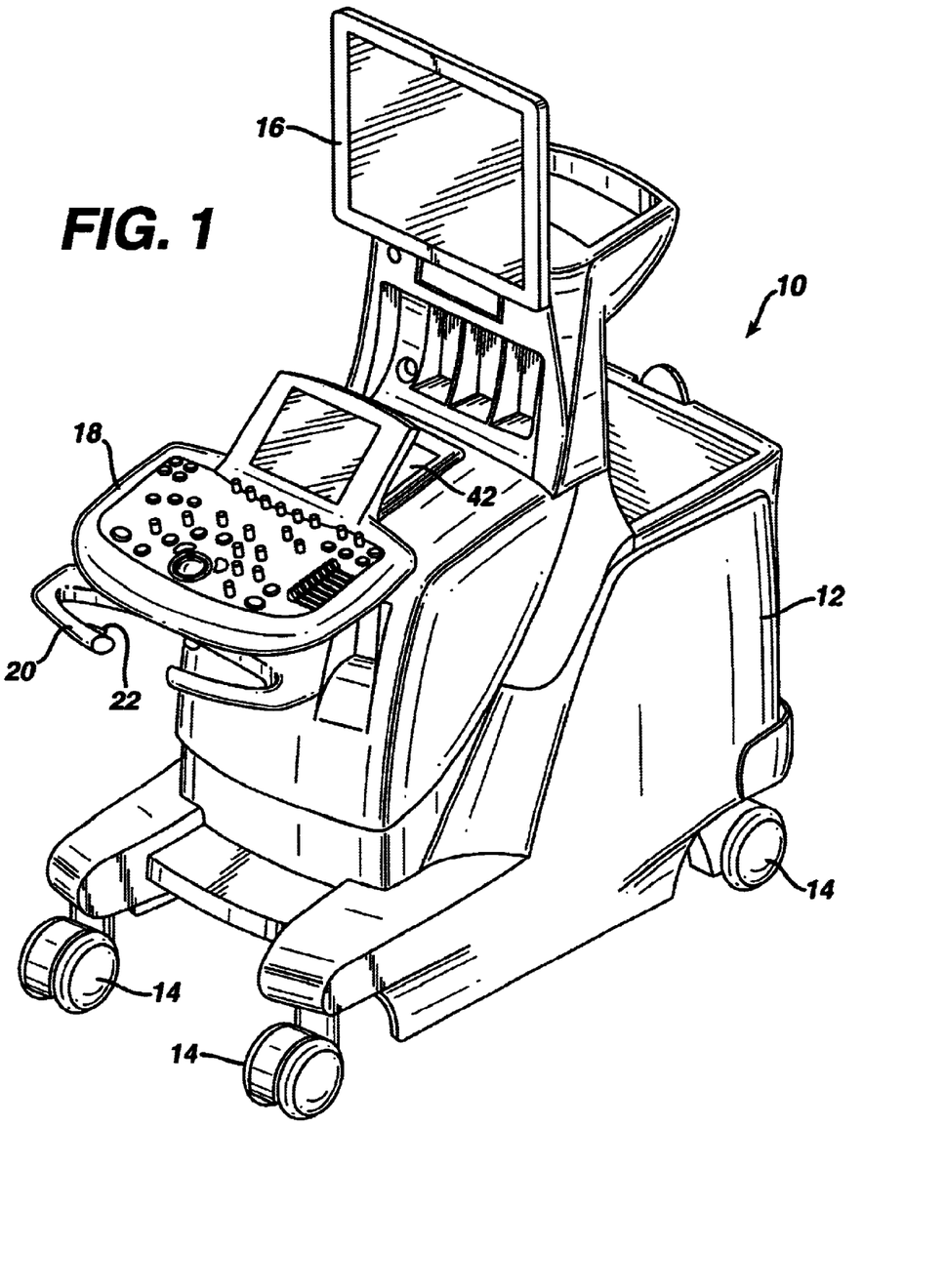
FIG. 1 illustrates a cart-borne ultrasound system in perspective.

Referring first to FIG. 1, a cart-borne ultrasound system 10 is shown in perspective. The cart includes an electronics bay 12 inside of which are located printed circuit boards for electronically processing received ultrasound signals. The ultrasound signals are processed to produce an image which is displayed on a display 16. The cart is mounted on wheels or casters 14 so that it can be rolled to a lab or a patient's bedside. In the front of the cart is a control panel 18, which contains a number of knobs, buttons, slide switches, and a trackball by which a user operates the ultrasound system. The control panel is mounted above a handle 20 which extends from the front of the ultrasound system. The handle 20 can be used to pull the cart to move it from one location to another. On the inside of the handle 20 is a lift release 22 which will be discussed below.

Figure 2:
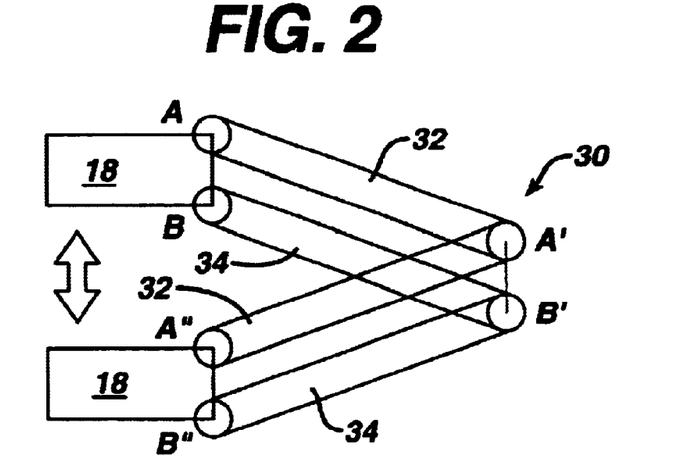
FIG. 2 illustrates the concept of a control panel lift mechanism of the present invention.

The concept of a lift mechanism of the present invention is shown in FIG. 2. A four bar linkage 30 is defined by four pivot points, A, B, A' and B'. Two of the bars are shown at 32 and 34, with the other two bars comprised by the pivot connections to the control panel 18 at A and B and the pivot connections to a base (not shown) at A' and B'. The linkage is shown in a raised position and a lowered position by the upper and lower locations of the control panel 18. The control panel moves between these positions as indicated by the large arrow. As can be seen by the block representation of the control panel 18, the angle of the control panel 18 does not change as the control panel is raised and lowered. In this drawing it is seen that the horizontal and vertical sides of the control panel block remain in this orientation in the raised and lowered and all intermediate positions.

Figure 3:
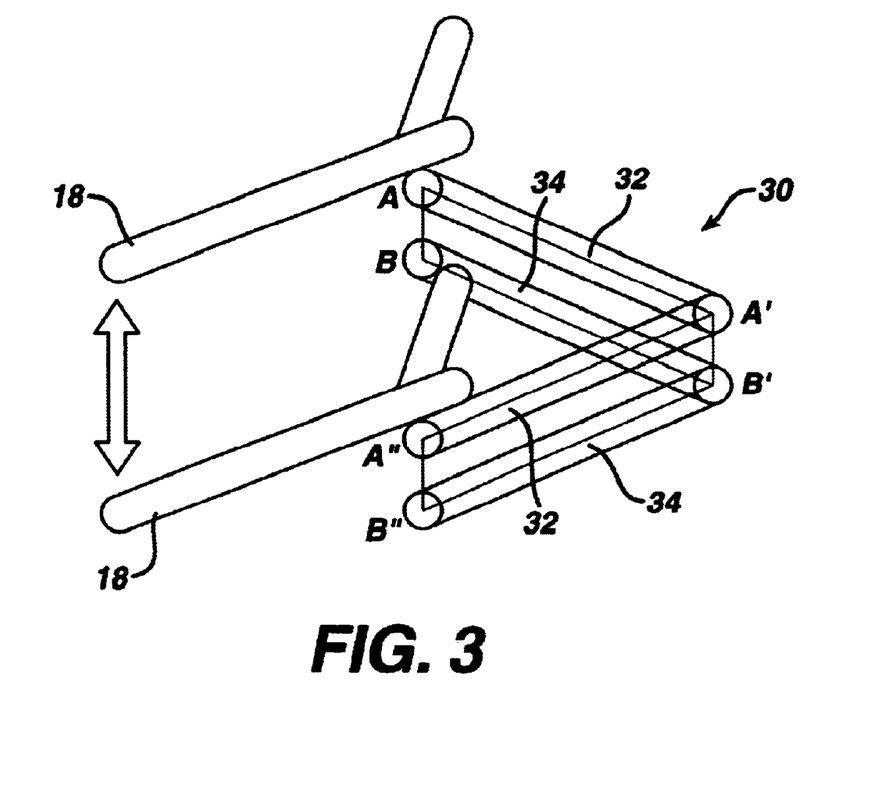
FIG. 3 shows the mechanism of FIG. 2 with a control panel in an end view.

FIG. 3 illustrates the four bar linkage 30 with the control panel 18 shown in a side view. As this drawing illustrates, the control panel is tilted at an angle which is comfortable for the user. Again it is seen that the angle of the control panel does not change between the raised and lowered positions by reason of the four bar linkage 30, which in the preferred embodiment is a parallelogram-shaped mechanism providing this benefit. The bars 30 and 32 remain parallel as the linkage moves, as do the axes between pivot points A–B and A'–B'.

Figure 4:
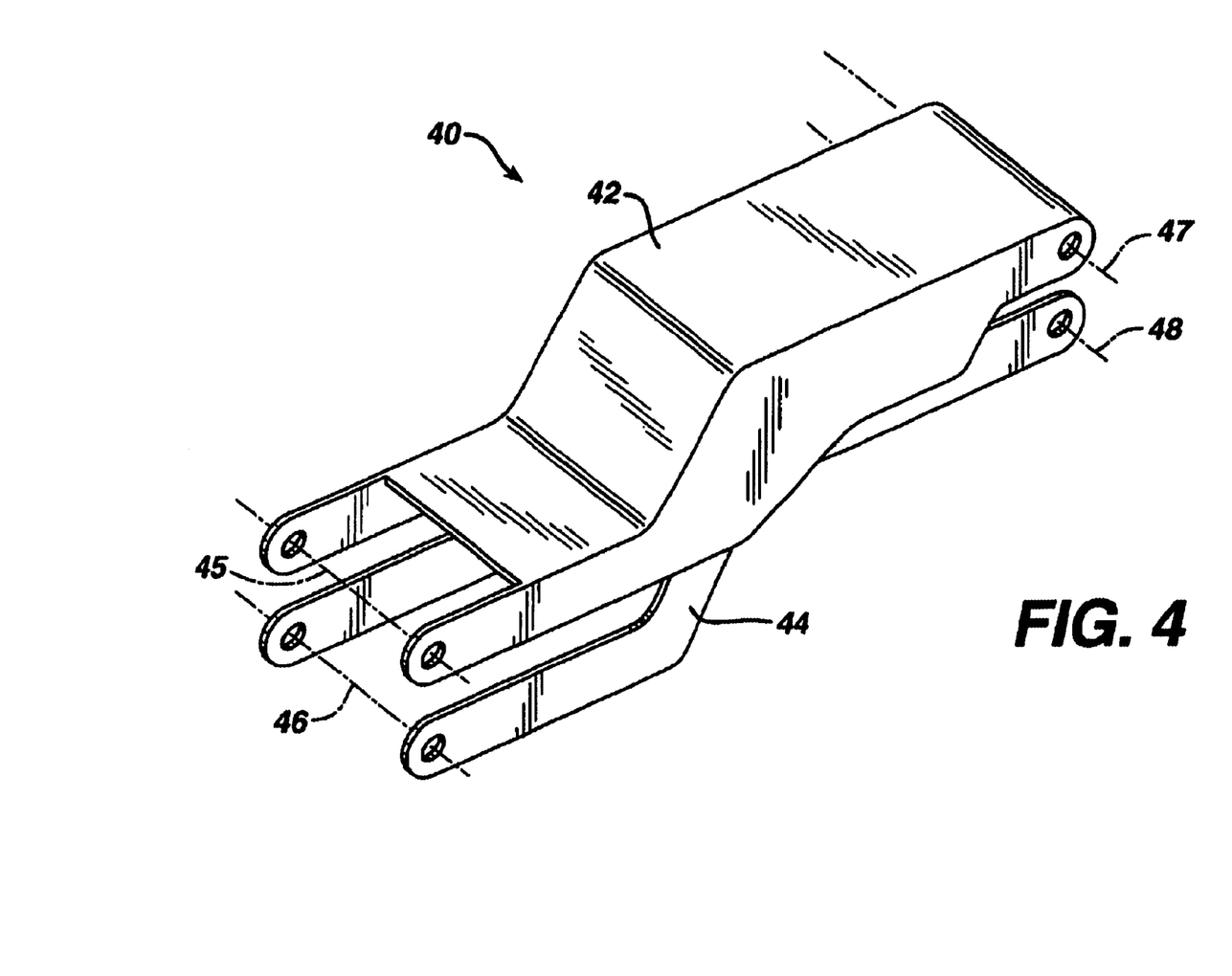
FIG. 4 illustrates the control panel lift mechanism of a constructed embodiment of the present invention.

FIG. 4 illustrates another articulating linkage 40 for a control panel which is suitable for use with the ultrasound system cart shown in FIG. 1. This linkage comprises a lift top cover 42 and a lift bottom cover 44. Each lift cover has two pivot holes at the front which are aligned on horizontal axes 45,46 and two pivot holes at the back which are aligned on horizontal axes 47,48. This lift cover assembly is partially visible behind the control panel 18 in FIG. 1. It is approximately 6 inches wide and 15 inches in length. The rear pivot holes at axes 47,48 are mounted to the ultrasound system cart and the control panel is mounted in the vicinity of front pivot holes at axes 45,46 as shown in the following drawings. If desired, beard covers can be provided below the linkage 40 to prevent the development of pinch points below the linkage when the control panel is elevated, as shown in concurrently filed U.S. patent [application Ser. No. ATL-295] incorporated herein by reference.

Figure 5A:
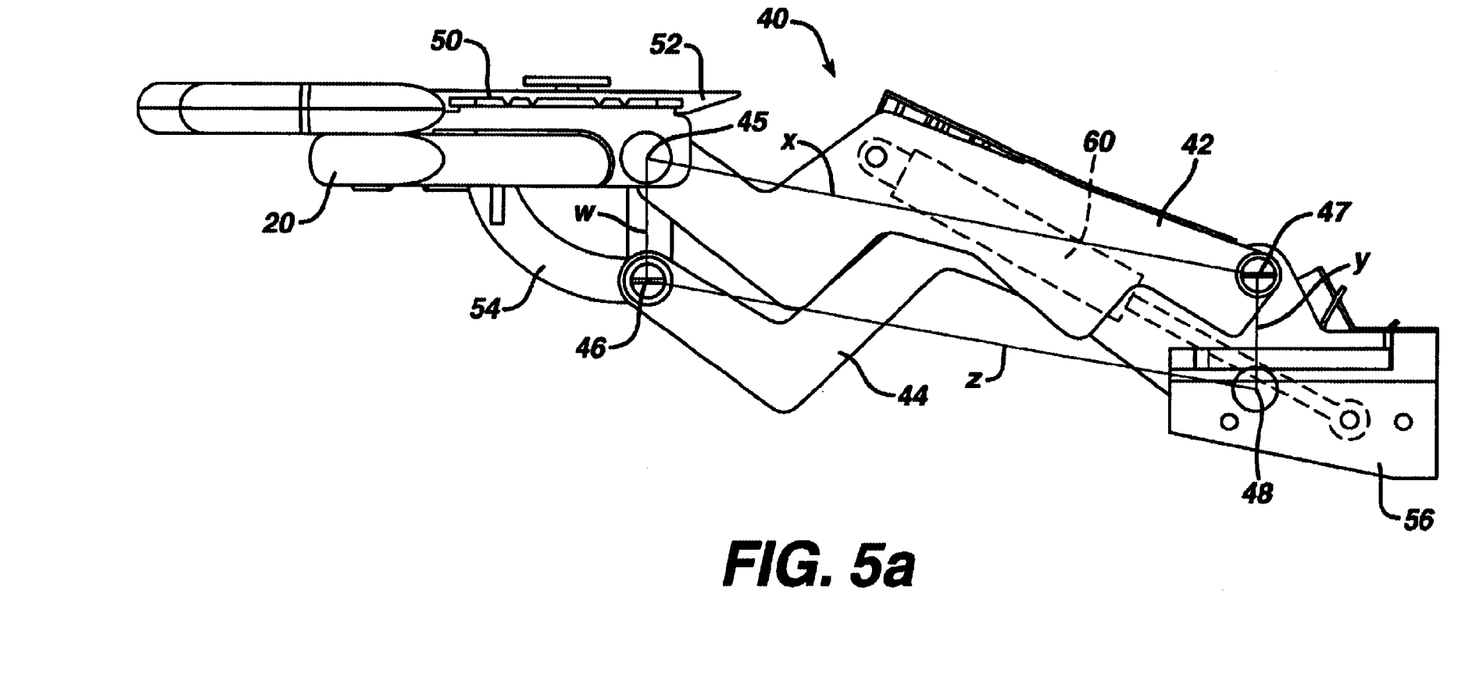
FIG. 5a illustrates a preferred lift mechanism in the raised position.

FIG. 5a illustrates the linkage assembly 40 in a raised position when attached to an ultrasound system cart. The two rear pivot points 47,48 of the assembly are connected to a lift base bracket 56, which is attached to the ultrasound system cart. The two forward pivot points are attached to a base for an ultrasound system control panel by attachment to an articulation base support 54 which supports the base. The base includes a bearing 50 on which is mounted a base slide 52. When the control panel is mounted on the base slide, it can slide forward and backward (left-right in the drawing) to an extended or retracted position selected by the system operator. Below the base the handle 20 is seen in a cutaway view.

As this drawing illustrates, the control panel can be raised and lowered by grasping the handle 20 to move the handle and control panel up and down, as both the handle and control panel are mounted on the articulating linkage 40. The articulating linkage is seen to be a four bar, parallelogram shaped linkage, as indicated by the lines w,x,y, and z drawn between the four pivot points 45,46,47,48 of the linkage.

Located beneath the lift top cover 42 is a positive lock, hydraulic piston 60 shown in phantom in FIG. 5*a*. The piston 60 supports the weight of the linkage, control panel and handle and is normally locked to maintain the positions of these elements. When the operator desires to raise or lower the control panel the handle 20 is grasped and the lift release 22 on the handle is depressed. The lift release could alternatively be operated by a foot pedal or located elsewhere on the cart. When the lift release 22 is depressed a valve is opened between two oil-filled compartments of the hydraulic piston. Oil then flows slowly from one compartment to the other, the direction of flow depending upon whether the control panel is being raised or lowered. The piston will extend or retract as the oil flows. When the control panel is at the desired height, the lift release is released by the operator, causing the valve of the piston to close, holding the piston and the control panel in its current elevation.

Figure 5B:
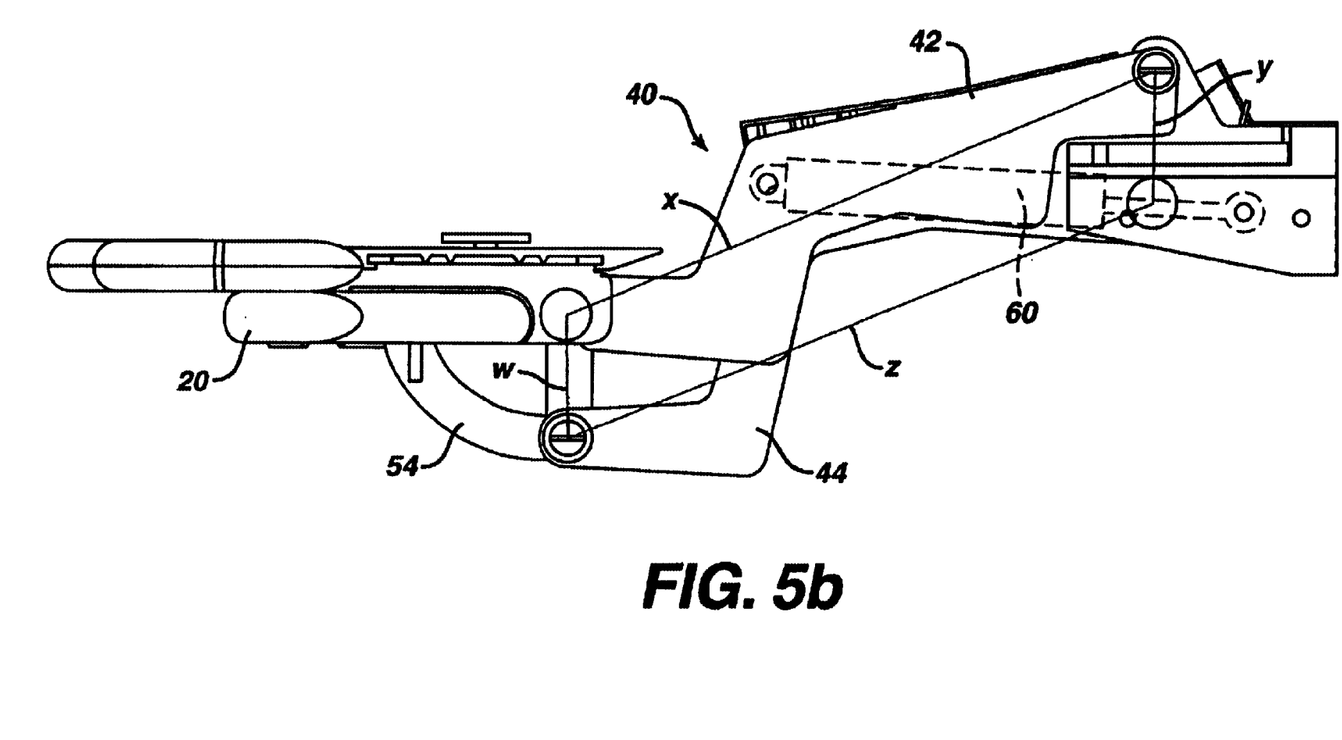
FIG. 5b illustrates a preferred lift mechanism in the lowered position.

FIG. 5*b* shows the linkage 40 and piston 60 when the control panel is in a lowered position. It is seen that the piston is in a retracted position in comparison to FIG. 5*a*. It is also seen that the angle of the control panel has not changed.

When the control panel is elevated such that the parallelogram w,x,y,z of the linkage 40 forms a rectangle, the control panel is at its most forward position relative to the cart and the center of the cart, which is approximately the vertical plane of the display 16. The control panel can be rolled forward even further toward the operator by sliding the control panel on the base slide 52. In this lowered position the control panel can be positioned over the lap of a system operator who is in the sitting position. As the control panel is raised from this elevation the sides x,z of the parallelogram will draw closer together and the control panel will simultaneously pivot up and rearward toward the center of the cart. In this raised position the control panel is retracted back to be more comfortable for use by an operator who is standing for the ultrasonic exam. In a constructed embodiment the control panel has approximately a ten inch range of vertical adjustment.

Various modifications of the illustrated embodiments will be readily apparent to those skilled in the art. For instance, the four bar linkage can be modified to have more than four pivot points, permitting more complex ranges of control panel movement. Instead of being manually raised and lowered, the control panel could be raised and lowered by motor control. The hydraulic piston can be a gas shock or replaced by other supporting devices such as springs or counterweights, in which case the elevation locking mechanism may comprise a mechanical device such as a detent or locking pin.

Figure 6A:
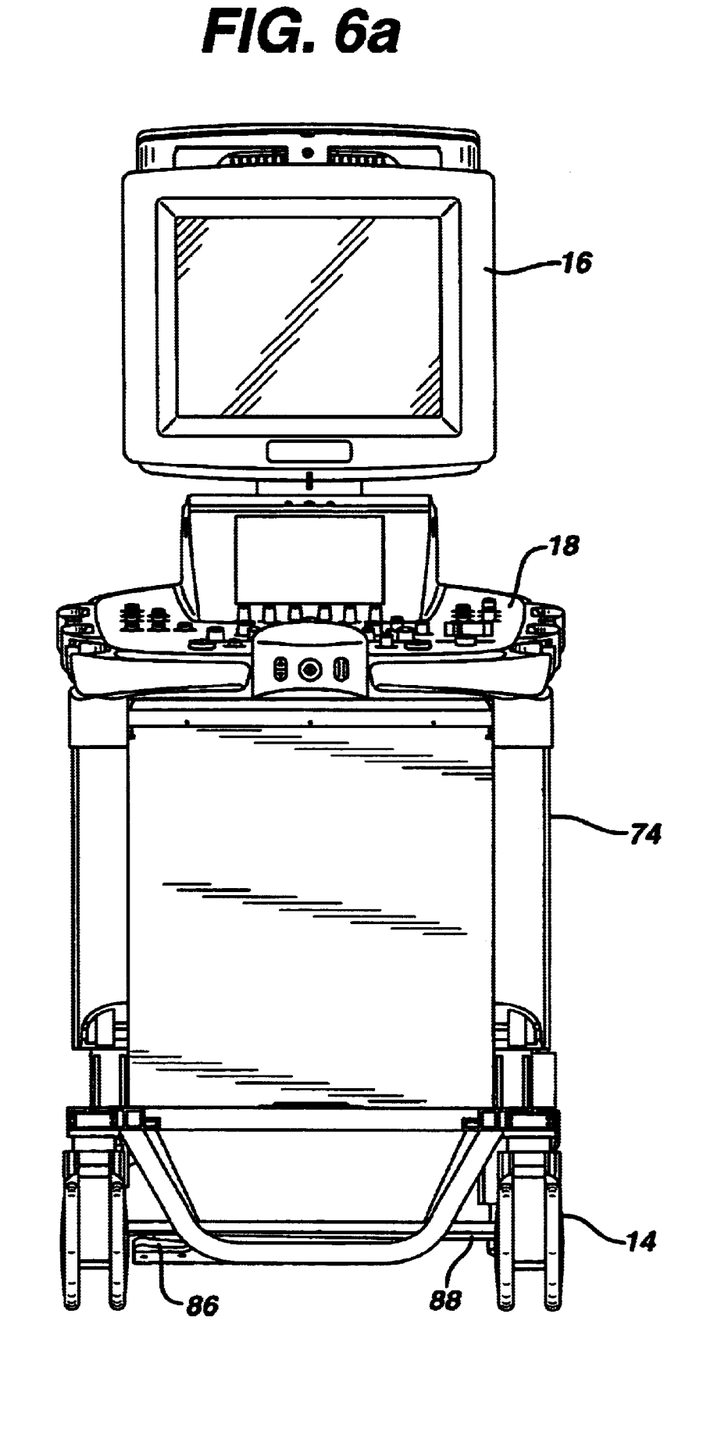
FIGS. 6a and 6b illustrate a further embodiment of the present invention in the lowered position.
Figure 6B:
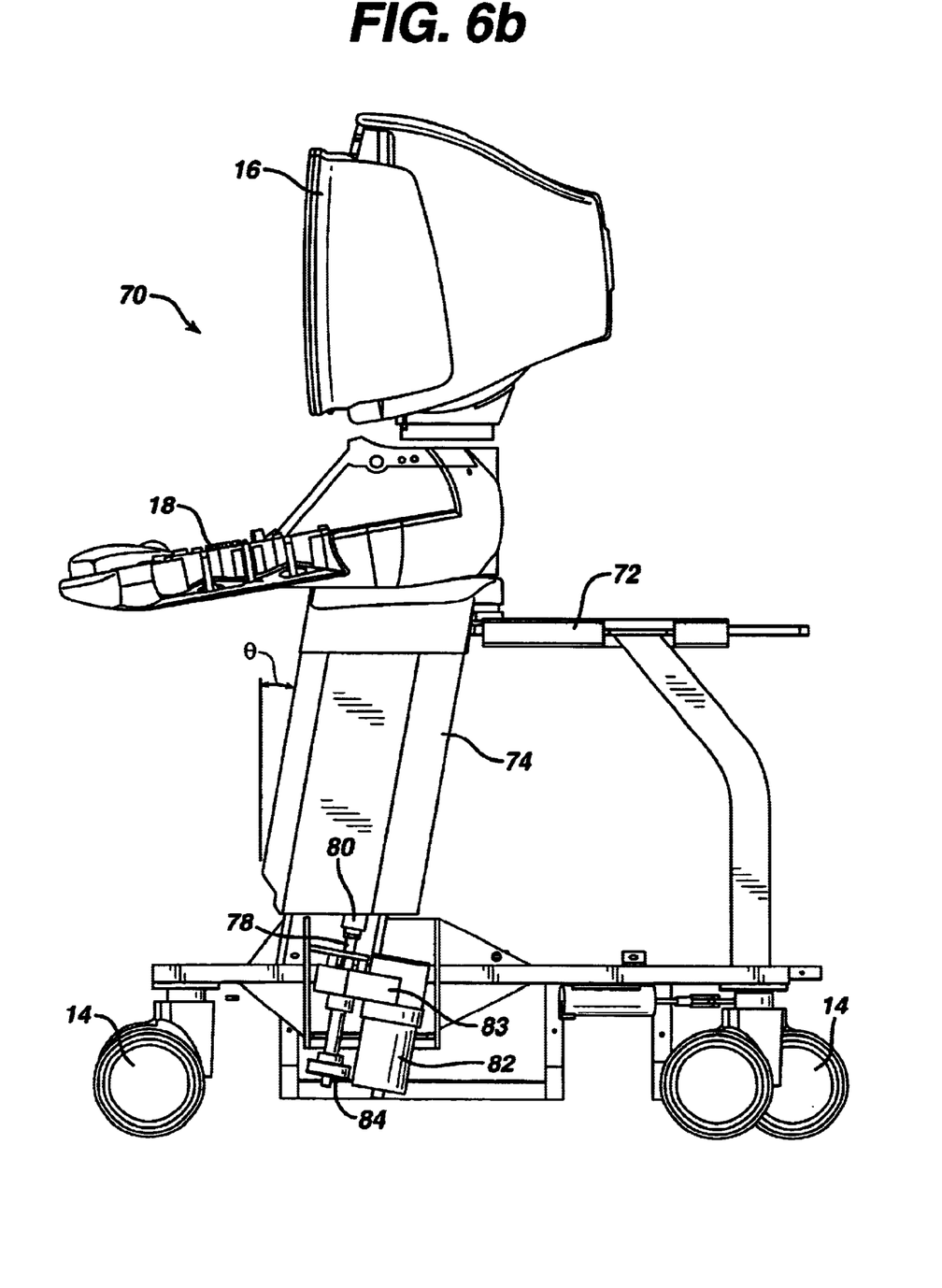
Figure 7A:
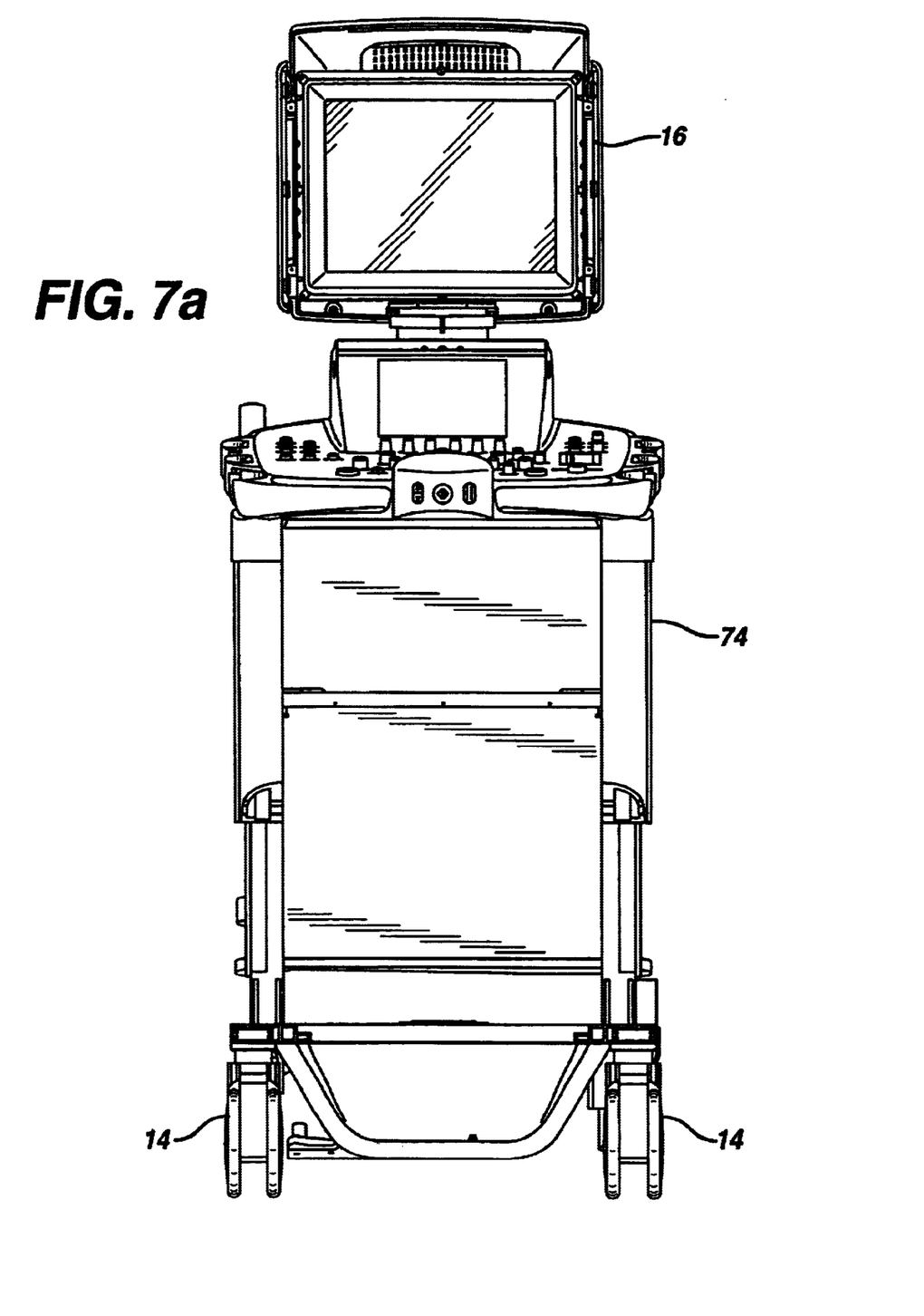
FIGS. 7a and 7b illustrate the embodiment of FIGS. 6a and 6b in the raised position.
Figure 7B:
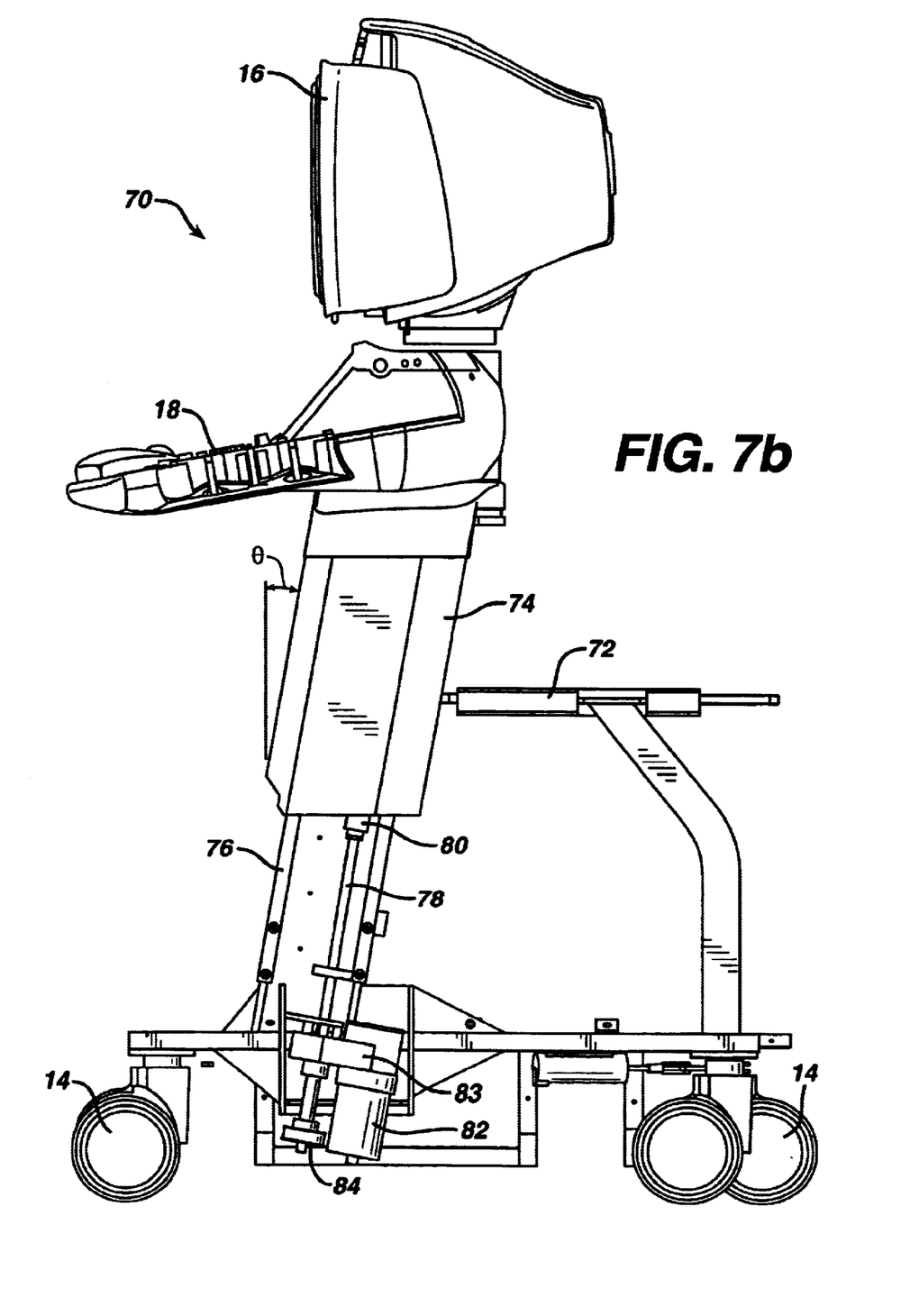

FIGS. 6*a*, 6*b*, 7*a* and 7*b* illustrate another embodiment of the present invention in which both the control panel and display are elevated and lowered by motor control. A cart-borne ultrasound system 70 includes a frame 72 mounted on wheels 14. The system display 16 and control panel 18 are supported on a yoke 74. The yoke 74 houses an articulation telescope bearing system which includes two shafts 78 which turn two threads 80. One shaft and thread is located on each side of the yoke 74. The shafts 78 are rotated by a ¼ hp DC motor 82, which is connected to one shaft 78 by a gearbox 83. Also connected to the gearbox is a pulley assembly 84, which is connected to a similar pulley assembly on the other side of the yoke by a belt 88. An idler 86 maintains the proper belt tension. FIGS. 6*a* and 6*b* illustrate the ultrasound system 70 with the control panel and display in the lowered position. When the shafts 78 are rotated by the motor, gearbox, and pulley mechanism, the threads turn and cause the yoke to raise, lifting the control panel and display to a greater height, as shown in FIGS. 7*a* and 7*b*. When the shafts are rotated in the opposite direction the control panel and display are lowered.

In accordance with the principles of the present invention, the articulation assembly does not move in the vertical direction, but at an acute angle θ with respect to vertical. This angled motion will cause the control panel and display to move forward toward the front of the cart when lowered, and to move backward away from the front of the cart when raised. Consequently, the control panel and display will be retracted back to better serve a standing user, and will move forward to extend over the lap of a sitting user. The angle of the control panel and display will not change as they are lowered, but will be maintained at the desired angle of comfort. In the illustrated embodiment the articulation mechanism is at approximately a 10° angle from vertical.

In a preferred embodiment the ultrasound system 70 includes a 12 volt battery which will power the articulation system when the power supply of the cart is not plugged in or energized. This enables the elevation of the control panel and display to be changed for transport of the system, without the need to power up the system's DC power supply from an a.c. source. The embodiment of FIGS. 6*a*–7*b* has been tested by lifting 150 pounds, and can be controlled by a simple pushbutton or rocker switch on the cart.

What is claimed is:

1. A cart-borne ultrasound system including a movable cart having a center; electronic circuitry located on the cart which processes ultrasound signals for the formation of ultrasound images, and a display coupled to the circuitry for the display of ultrasound images, comprising:

a control panel coupled to the electronic circuitry for user control of the ultrasound system; and an articulation mechanism mounted on the cart and coupled to the control panel which enables the control panel to be articulated vertically while maintaining a substantially constant angle of inclination, the articulation mechanism further enabling the control panel to move closer to the center of the cart in the highest position and further from the center of the cart in the lowest position.

2. The cart-borne ultrasound system of claim 1, wherein the control panel further includes a plurality of user controls coupled to the electronic circuitry by which a user can control the operation of the ultrasound system.

3. The cart-borne ultrasound system of claim 2, wherein the articulation mechanism enables the control panel to be articulated independently of the display.

4. The cart-borne ultrasound system of claim 1, wherein the articulation mechanism comprises four pivot points defining the corners of a parallelogram.

5. The cart-borne ultrasound system of claim 4, wherein two of the pivot points of the articulation mechanism are coupled to the control panel and two of the pivot points of the articulation mechanism are coupled to the cart.

6. The cart-borne ultrasound system of claim 1, further comprising a counterbalance coupled to the cart and to the control panel to support at least some of the weight of the control panel when the height of the control panel is adjusted.

7. The cart-borne ultrasound system of claim 6, wherein the counterbalance comprises a spring.

8. The cart-borne ultrasound system of claim 6, wherein the counterbalance comprises a hydraulic piston.

9. The cart-borne ultrasound system of claim 6, wherein the counterbalance comprises a counterweight.

10. The cart-borne ultrasound system of claim 1, wherein the articulation mechanism comprises a lift mechanism which moves the control panel in a direction which is at an acute angle with respect to vertical.

11. The cart-borne ultrasound system of claim 10, wherein the lift mechanism raises and lowers the control panel in a straight line direction.

12. The cart-borne ultrasound system of claim 11, wherein the lift mechanism is motor driven.

13. The cart-borne ultrasound system of claim 12, wherein the lift mechanism further includes two threads and two motor driven shafts.

14. The cart-borne ultrasound system of claim 12, wherein the ultrasound system further comprises a battery which powers the motor driven lift mechanism.

15. A cart-borne ultrasound system including a movable cart having a center, ultrasound electronics located on the cart which processes ultrasound signal to form ultrasound image signals, and a display device located on the cart and coupled to the ultrasound electronics for the display of ultrasound images, comprising:

a control panel which provides user controls for the control of operation of the ultrasound system; and an articulating linkage coupled to the control panel for enabling the control panel to move vertically while maintaining the inclination of the control panel.

16. The cart-borne ultrasound system of claim 15, wherein the articulating linkage comprises a four bar linkage having at least four pivot points.

17. The cart-borne ultrasound system of claim 16, wherein the four bar linkage comprises a parallelogram-shaped mechanism coupled to the control panel and the cart, and having four pivot points which define a parallelogram, two of the pivot pints being coupled to the control panel and two of the pivot points being coupled to the cart.

18. The cart-borne ultrasound system of claim 17, wherein the articulating parallelogram-shaped mechanism maintains a substantially constant angle of inclination of the control panel as the control panel is raised and lowered.

19. The cart-borne ultrasound system of claim 17, wherein the articulating parallelogram-shaped mechanism causes the control panel to move toward the center of the cart as the control panel is raised, and away from the center of the cart as the control panel is lowered.

20. The cart-borne ultrasound system of claim 17, wherein the articulating parallelogram-shaped mechanism comprises a first articulating parallelogram-shaped device located on one side of the control panel, and a second articulating parallelogram-shaped device located on the other side of the control panel, wherein the first and second articulating parallelogram-shaped devices articulate in unison.

21. The cart-borne ultrasound system of claim 15, further comprising a supporting device which supports at least some of the weight of the control panel as the control panel is articulated.

22. The cart-borne ultrasound system of claim 21, wherein the supporting device comprises a hydraulic piston.

23. The cart-borne ultrasound system of claim 21, wherein the supporting device comprises a spring.

24. The cart-borne ultrasound system of claim 21, wherein the supporting device comprises a counterbalance.

25. A cart-borne ultrasound system including a movable cart having a center, ultrasound electronics located on the cart which processes ultrasound signal to form ultrasound image signals, and a display device located on the cart and coupled to the ultrasound electronics for the display of ultrasound images, comprising:

a control panel which provides user controls for the control of operation of the ultrasound system; and an articulating linkage coupled to the control panel for enabling the control panel to move vertically independently of the display device while maintaining the inclination of the control panel.

* * * * *